United States Patent
Adiga et al.

(10) Patent No.: US 8,588,503 B2
(45) Date of Patent: Nov. 19, 2013

(54) SYSTEM AND METHOD FOR DETECTING AND ELIMINATING ONE OR MORE DEFOCUSED OR LOW CONTRAST-TO-NOISE RATIO IMAGES

(75) Inventors: Umesha Adiga, Clifton Park, NY (US); Ali Can, Troy, NY (US); Xudong Li, Somerset, NJ (US); Dirk R. Padfield, Albany, NY (US); Jens Rittscher, Ballston Lake, NY (US); Elizabeth P. Roquemore, Cardiff (GB)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 115 days.

(21) Appl. No.: 12/993,180

(22) PCT Filed: May 29, 2009

(86) PCT No.: PCT/SE2009/050623
§ 371 (c)(1),
(2), (4) Date: Nov. 17, 2010

(87) PCT Pub. No.: WO2009/145723
PCT Pub. Date: Dec. 3, 2009

(65) Prior Publication Data
US 2011/0069905 A1 Mar. 24, 2011

Related U.S. Application Data

(60) Provisional application No. 61/057,212, filed on May 30, 2008.

(51) Int. Cl.
*G06K 9/00* (2006.01)
*G06K 9/78* (2006.01)

(52) U.S. Cl.
USPC .......................................... 382/133; 382/216

(58) Field of Classification Search
None
See application file for complete search history.

(56) References Cited

U.S. PATENT DOCUMENTS 6,075,905 A * 6/2000 Herman et al. ............... 382/284
7,298,876 B1 * 11/2007 Marshall et al. .............. 382/128
(Continued)

FOREIGN PATENT DOCUMENTS

WO  WO 2007/028944  3/2007
WO  WO 2007/121454  10/2007

OTHER PUBLICATIONS

Genovesio, A., et al., "Multiple Particle Tracking in 3-D+t Microscopy: Method and Application to the Tracking of Endocytosed Quantum Dots", IEEE Trans. Image Proc., (2006), 15(5):1062-1070.

(Continued)

*Primary Examiner* — Nancy Bitar (57) ABSTRACT

This invention, which provides a method for detecting a corruption in an image acquired from a biological sample, includes: providing at least one image of at least one cell; generating the image of the at least one cell over a period of time; determining if the at least one image of the at least one cell is corrupted; applying a wavelet transform, Fourier transform, or other frequency decomposing transform to the at least one image to decompose the at least one image into a plurality of sub-images, wherein the plurality of sub-images have a plurality of low frequency channels, a plurality of middle frequency channels and a plurality of high frequency channels; calculating a ratio based on an energy level of the plurality of low frequency channels and the plurality of middle frequency channels; and removing the at least one image of at least one cell if the at least one image is corrupted.

8 Claims, 8 Drawing Sheets

(56) References Cited

U.S. PATENT DOCUMENTS

| | | | |
|---|---|---|---|
| 7,680,308 B2* | 3/2010 | Dale | 382/128 |
| 8,041,090 B2* | 10/2011 | Alexandrov et al. | 382/128 |
| 2003/0012420 A1 | 1/2003 | Verwoerd et al. | |
| 2010/0086189 A1* | 4/2010 | Wang et al. | 382/132 |

OTHER PUBLICATIONS

Li, et al., "Online tracking of migrating and proliferating cells imaged with phase-contrast microscopy", Proc. CVPRW. (2006), 65-72.

Olivo, J., "Automatic Detection of Spots in Biological Images by a Wavelet-Based Selective Filtering Technique", IEEE, (1996), 311-314.

Padfield, D., et al., "Spatio-Temporal Cell Cycle Analysis using 3D Level Set Segmentation of Unstained Nuclei in Line Scan Confocal Images", IEEE ISBI, Arlington, VA (Apr. 2006).

Padfield, D., et al., "Defocus and Low CNR Detection for Cell Tracking Applications", MIAAB, New York, NY (Sep. 2008).

Padfield, D., et al., "Spatio-Temporal Cell Segmentation and Tracking for Automated Screening", IEEE ISBI, p. 376-379 (May 2008).

Porter, R., et al., "A Robust Automatic Clustering Scheme for Image Segmentation using Wavelets", IEEE Transactions on Image Processing, (1996), 5(4):pp. 662-665.

* cited by examiner

SYSTEM AND METHOD FOR DETECTING AND ELIMINATING ONE OR MORE DEFOCUSED OR LOW CONTRAST-TO-NOISE RATIO IMAGES

CROSS-REFERENCE TO RELATED APPLICATIONS

This application is a filing under 35 U.S.C. §371 and claims priority to international patent application number PCT/SE2009/050623 filed May 29, 2009, published on Dec. 3, 2009 as WO 2009/145723, which claims priority to U.S. provisional patent application No. 61/057,212 filed on May 30, 2008.

FIELD OF THE INVENTION

The present invention relates to a system and method for detecting and eliminating one or more abnormal images acquired from biological samples.

BACKGROUND OF THE INVENTION

Generally, the detailed mechanisms by which most genes, cells and viruses function in humans and other organisms are relatively unknown, despite the fact that there have been successful genomic sequencing programs and other extensive functional genomics efforts. Consequently, there is a need for screening approaches that enable high-throughput examination and elucidation of gene functions in a relevant physiological environment.

High-throughput, automated fluorescence microscopy makes it possible to screen and analyze the functions of hundreds of thousands of gene products in the context of the cell. Because microscopy has the potential to yield significantly more sub-cellular information than other detection methods, the term 'high content' has been adopted to describe screens and assays that are detected and quantified using automated imaging platforms. Both image acquisition and image analysis can be automated and then optimized to maximize throughput on high-content analysis systems. Two core components of the computational tools required for automated image analysis are the segmentation and positional tracking of individual cells.

Motility and division are two fundamental cell behaviors that are of great importance in a number of areas of research, including oncology, immunology, and developmental biology. While these behaviors have unique analysis requirements, they also share several significant analysis challenges. Examination of these behaviors requires time-lapse imaging Implementation of time-lapse imaging for large-scale experimentation poses challenges with respect to finding assay, imaging, and analysis parameters that will be optimal across the wide variety of treatment conditions and behavioral phenotypes represented in a particular data set. Another challenge is the frequent problem of low contrast-to-noise ratios in acquired images. In live-cell time-lapse experiments, poor contrast-to-noise ratios often arise from deliberate reduction of dye concentrations in order to avoid unwanted toxic side-effects such as DNA-binding, which inhibits DNA replication in living cells. An added challenge is that automated focus mechanisms occasionally fail under the demands of high-speed acquisition protocols. Model systems also typically contain far more targets (cells) than are monitored with common surveillance applications. Specific biological events such as mitosis also need to be handled.

Existing analysis routines for cell tracking can be roughly divided into two main approaches: independent detection with subsequent data association, and model-based tracking. In the publication by Li et al., entitled "Online tracking of migrating and proliferating cells imaged with phase-contrast microscopy", the aforementioned approaches are combined by both segmenting each frame separately and using a multi-target tracking system using model propagation with level sets and a stochastic motion filter, which is hereby incorporated by reference. *Proc. CVPRW*. (2006) pages 65-72. In another publication by Padfield et al., entitled "Spatio-temporal Cell Cycle Analysis using 3D level set segmentation of unstained nuclei in line scan confocal images", another approach is utilized for the tracking task as a spatio-temporal segmentation task, which is hereby incorporated by reference. *IEEE ISBI*, Arlington, Va. (April 2006).

There is a need for a system and method that detects corruptions in images of biological materials to enable elimination of poor images and provide better segmentation and tracking of objects comprising the biological material.

SUMMARY OF THE INVENTION

The present invention has been accomplished in view of the above-mentioned technical background, and it is an object of the present invention to provide a system and method for detecting a corrupted image acquired from a biological sample.

In a preferred embodiment of the invention, a method for detecting a corrupted image acquired from a biological sample includes: providing at least one image of at least one cell; generating the image of the at least one cell over a period of time; determining if the at least one image of the at least one cell has corruptions; applying a wavelet transform, Fourier transform, or other frequency decomposing transform to the at least one image to decompose the at least one image into a plurality of sub-images, wherein the plurality of sub-images have a plurality of low frequency channels, a plurality of middle frequency channels and a plurality of high frequency channels; calculating a ratio based on an energy level of the plurality of low frequency channels and the plurality of middle frequency channels; and removing the at least one image of at least one cell if the at least one image has the corruptions.

In another preferred embodiment of the invention, a system for detecting a corruption in an image acquired from a biological sample is disclosed. An image transmitting device configured to transmit at least one image of at least one cell to an image receiving device. The image receiving device is configured to: provide at least one image of the at least one cell; determine if the at least one image of the at least one cell has corruptions; apply a wavelet transform, Fourier transform, or other frequency decomposing transform to the at least one image to decompose the at least one image into a plurality of sub-images, wherein the plurality of sub-images have a plurality of low frequency channels, a plurality of middle frequency channels and a plurality of high frequency channels; calculate a ratio based on an energy level of the plurality of low frequency channels and the plurality of middle frequency channels; and either remove the at least one image of at least one cell if the at least one image is corrupted, or segment and track objects within the image of the at least one cell if the at least one image does not have the corruption.

In yet another preferred embodiment of the invention, an apparatus for detecting a corruption in an image is disclosed. An image receiving device is configured to: provide at least one image of the at least one cell; determine if the at least one image of the at least one cell is corrupted; apply a wavelet transform, Fourier transform, or other frequency decomposing transform to the at least one image to decompose the at least one image into a plurality of sub-images, wherein the plurality of sub-images have a plurality of low frequency channels, a plurality of middle frequency channels and a plurality of high frequency channels; calculate a ratio based on an energy level of the plurality of low frequency channels and the plurality of middle frequency channels; and remove the at least one image of at least one cell if the at least one image has the corruption.

In another preferred embodiment of the invention, a computer-implemented image processing method for detecting a corruption in an image of biological material is disclosed. The method includes: providing at least one image of at least one cell; determining if the at least one image has the corruption; apply a wavelet transform, Fourier transform, or other frequency decomposing transform to the at least one image to decompose the at least one image into a plurality of sub-images, wherein the plurality of sub-images have a plurality of low frequency channels, a plurality of middle frequency channels and a plurality of high frequency channels; calculate a ratio based on an energy level of the plurality of low frequency channels and the plurality of middle frequency channels; and removing the at least one image of at least one cell if the at least one image has the corruption.

BRIEF DESCRIPTION OF THE DRAWINGS

These and other advantages of the present invention will become more apparent as the following description is read in conjunction with the accompanying drawings, wherein.

DETAILED DESCRIPTION OF THE INVENTION

The presently preferred embodiments of the invention are described with reference to the drawings, where like components are identified with the same numerals. The descriptions of the preferred embodiments are exemplary and are not intended to limit the scope of the invention.

Figure 1:
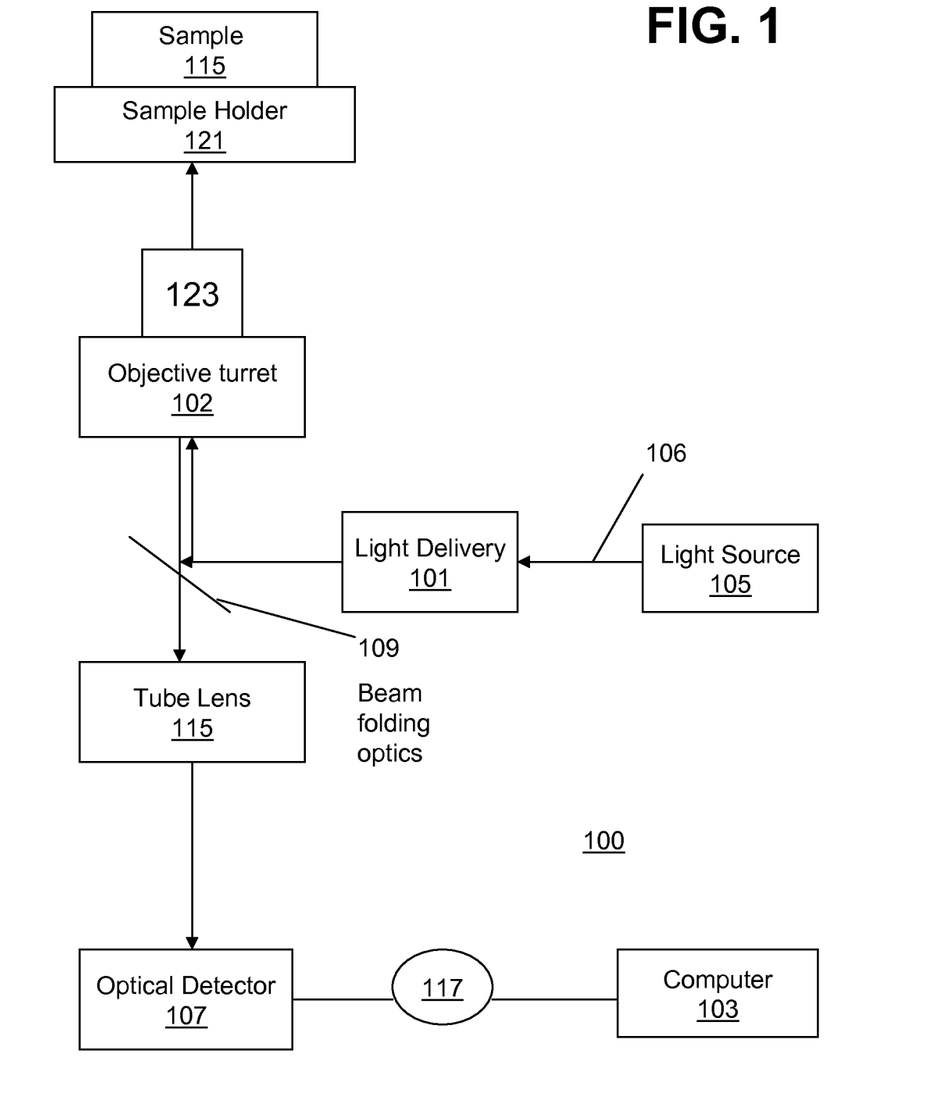
FIG. 1 is a block diagram of a system for detecting a corruption in a biological material in accordance with an embodiment of the invention.

FIG. 1 illustrates a block diagram of the essential components of a typical digital microscope system that includes a system for detecting a corruption in an image of a biological material. This automated digital microscope system 100 includes: a light source 105, propagation/beam shaping optics (light delivery) 101, beam folding optics 109, an objective turret 102 holding objective lens 123, sample 115, sample positioning stage 113, communication link 117, imaging optics (tube lens) 108, an optical detector 107, and an optional computer 103.

The light source 105 may be a lamp, a laser, a plurality of lasers, a light emitting diode (LED), a plurality of LEDs, or any type of light source known to those of ordinary skill in the art that generates a light beam 106. The light beam 106 is directed by the propagation/beam-shaping optics 101, beam-folding optics 109 and objective lens 123 to illuminate the sample 115. Sample 115 includes biological material, such as cells, proteins, small molecules, oligonucleotides, proteins (e.g. enzymes, antibodies, etc.), tissue specimens, DNA, RNA and other typical biological materials. The light signal emanating from the sample 115 is collected by the objective lens 123 and imaging optics 108 to form an image on the optical detector 107. The optical detector 107 may be a photomultiplier tube, a charged coupled device (CCD), a complementary metal-oxide semiconductor (CMOS) image detector or any optical detector utilized by those of ordinary skill in the art. Optical detector 107 is electrically or wirelessly connected by the communication link 117 to the computer 103. In another embodiment, the optical detector 107 may be replaced with the typical microscope eyepiece or oculars that work with objective lens mounted in the objective turret 102 to further magnify the intermediate image so that specimen details can be observed. Sample 115 is contained in the sample holder 121, which may be referred to as a typical micro titer plate, a microscope slide, a microwell plate, a chip, plate of glass, Petri dish, plastic, or silicon or any type of typical holder. The microwell plate may have 96 wells, 384 wells, 1534 wells or any typical amount of wells in a microwell plate having any height, width, length, base, well diameter, well depth known to those of ordinary skill in the art. There may also be two or more sample specimen holders 121.

In another embodiment, the microscope system 100 may be electrically or wirelessly connected by a communication link 117 to the conventional computer 103. The communication link 117 may be any network that is able to facilitate the transfer of data between the automated microscope system 100 and the computer 103, such as a local access network (LAN), a wireless local network, a wide area network (WAN), a universal service bus (USB), an Ethernet link, fiber-optic or the like. The microscope may also have a plurality of objective lenses 123. The computer 103 may be referred to as an image receiving device 103 or image detection device 103. In another embodiment of the invention, image receiving device 103 may be located inside of the image transmitting device 100. The image receiving device 103 acts as a typical computer, which is capable of receiving an image of the sample 115 from the optical detector 107, then the image receiving device 103 is able to display, save or process the image by utilizing a standard image processing software program, analysis routine, algorithm or equation. Also, the computer 103 may be a personal digital assistant (PDA), laptop computer, notebook computer, mobile telephone, hard-drive based device or any device that can receive, send and store information through the communication link 117. Although one computer is utilized in this invention, a plurality of computers may be utilized in place of computer 103.

The microscope system 100 has been depicted schematically in FIG. 1 with only the essential components highlighted. It will be obvious to a person skilled in the art of microscopy that the block diagram describes all microscopes using an objective lens. Examples include, but are not limited to, conventional wide-field microscope, fluorescent microscope, traditional confocal microscope, line scanning confocal microscope. These types of microscopes may be augmented with automation equipment to serve different applications, such as high-throughput screening. However, they are not precluded from the scope of this invention. Also, the microscope system 100 may also be the INCELL™ Analyzer 1000 or 3000 manufactured by GE Healthcare in Piscataway, N.J.

Figure 2:
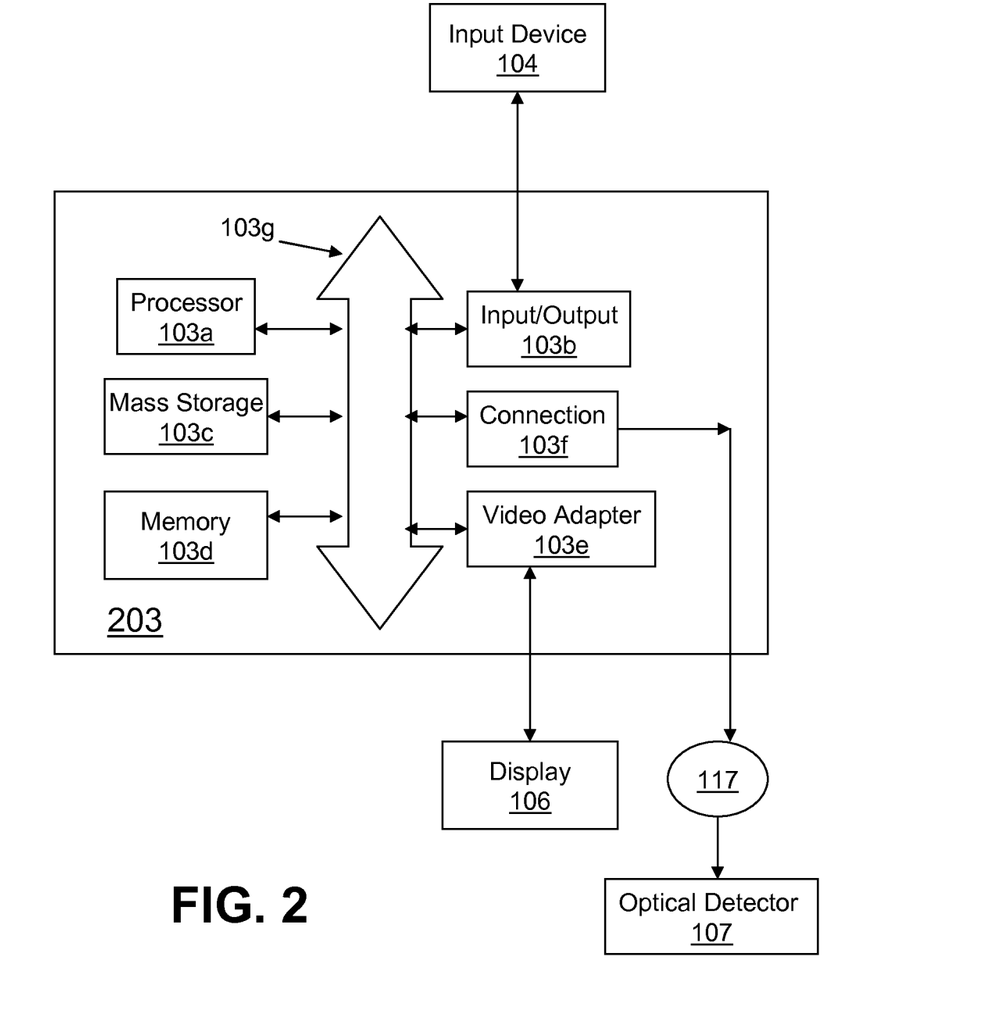
FIG. 2 is a schematic diagram of an image receiving device of FIG. 1 in accordance with the invention.

FIG. 2 illustrates a schematic diagram of the image receiving device of the corruption detection system of FIG. 1. Image or imaging receiving device 103 includes the typical components associated with a conventional computer. Image receiving device 103 may also be stored on the image transmitting system 100. The image receiving device 103 includes: a processor 103a, an input/output (I/O) controller 103b, a mass storage 103c, a memory 103d, a video adapter 103e, a connection interface 103f and a system bus 103g that operatively, electrically or wirelessly, couples the aforementioned systems components to the processor 103a. Also, the system bus 103g, electrically or wirelessly, operatively couples typical computer system components to the processor 103a. The processor 103a may be referred to as a processing unit, a central processing unit (CPU), a plurality of processing units or a parallel processing unit. System bus 103g may be a typical bus associated with a conventional computer. Memory 103d includes a read only memory (ROM) and a random access memory (RAM). ROM includes a typical input/output system including basic routines, which assists in transferring information between components of the computer during start-up.

Input/output controller 103b is connected to the processor 103a by the bus 103g, where the input/output controller 103b acts as an interface that allows a user to enter commands and information into the computer through an automatic corruption detection means such as an optional graphical user interface (GUI) and input device 104, such as a keyboard and pointing devices. The typical pointing devices utilized are joysticks, mouse, game pads or the like. A display 106 is electrically or wirelessly connected to the system bus 103g by the video adapter 103e. Display 106 may be the typical computer monitor, plasma television, liquid crystal display (LCD) or any device capable of displaying characters and/or still images generated by a computer 103. Next to the video adapter 103e of the computer 103, is the connection interface 103f. The connection interface 103f may be referred to as a network interface, which is connected, as described above, by the communication link 117 to the optical detector 107. Also, the image receiving device 103 may include a network adapter or a modem, which enables the image receiving device 103 to be coupled to other computers.

Above the memory 103d is the mass storage 103c, which includes: 1. a hard disk drive component (not shown) for reading from and writing to a hard disk, and a hard disk drive interface (not shown), 2. a magnetic disk drive (not shown) and a hard disk drive interface (not shown) and 3. an optical disk drive (not shown) for reading from or writing to a removable optical disk such as a CD-ROM or other optical media and an optical disk drive interface (not shown). The aforementioned drives and their associated computer readable media provide non-volatile storage of computer-readable instructions, data structures, program modules and other data for the computer 103. Also, the aforementioned drives include the technical effect of having an algorithm, analysis routine, software or equation for determining if corruption or problems exist in an image of a biological material, which will be described in the flow chart of FIG. 3. The term corruption, problem or faulty used in this application indicates that the image is defocused or has low contrast-to-noise ratio and can therefore lead to segmentation/tracking failures.

The software has a corruption detection graphical user interface (GUI). The corruption detection graphical user interface is a specially programmed GUI that has some of the same functionality as a typical GUI, which is a software program designed to allow a computer user to interact easily with the computer 103.

Figure 3:
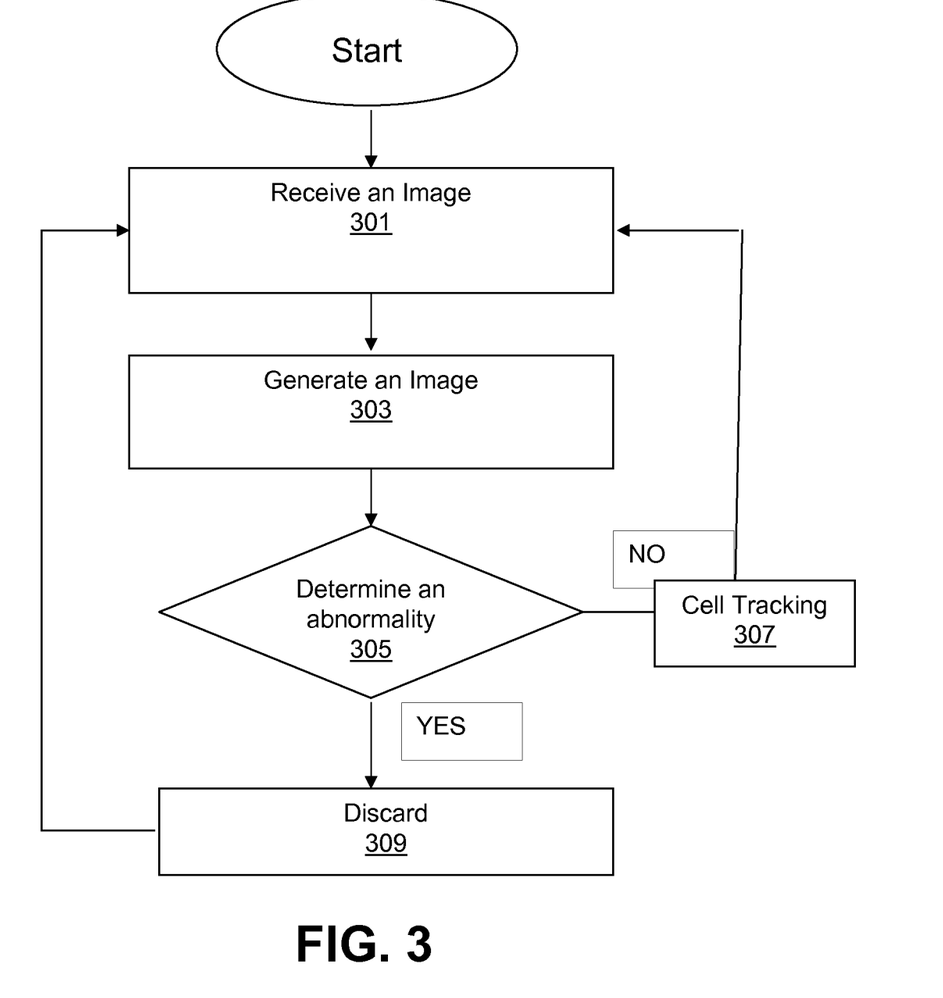
FIG. 3 is a flow-chart that depicts how the detection of a corruption in an image acquired from a biological sample, using the system of FIG. 1, is utilized in accordance with the invention.

FIG. 3 depicts a flow chart of how corruption of an image of a biological sample is detected in a software application. This description is in reference to an image of one cell, but this description also applies to a plurality of images of one cell or a number of cells being detected by the microscope system 100. A user inserts the biological sample (e.g. cell or plurality of cells) into the microscope system 100, where an image of the sample is transferred by the optical detector 107 through the communication link 117 by the connection interface 103f (FIG. 2) where the image is received at the image receiving device 103 at block 301.

At block 303, the user employs a pointing device 104 to generate one or more images of a population consisting of at least one cell over a period of time. Exposure times for a single image could range from 1 to 100 milliseconds in a typical assay, depending on the detection system. In a typical live-cell time-course assay, a series of such images is collected at specified intervals over a defined period of time, which could range from 1-100 milliseconds to several days. The acquired data of the cell could comprise an image of a single cell or a plurality of cells having a plurality of images. At block 305, the user utilizes the pointing device 104 on the corruption detection graphical user interface to point to an icon that says, for example START, which allows the user to initiate the determination if the image of the biological material or cell is corrupted. As stated above, this corruption detection graphical user interface and software is on a processor of the image receiving device 103. If the image does not exhibit an corruption, then the process goes through the normal segmentation and cell tracking procedure at block 307 the returns to block 301 where another image is received in sequence. However, if there is a determination that there is a corrupted image, then the image is discarded, and the next image is processed.

Figure 4A:
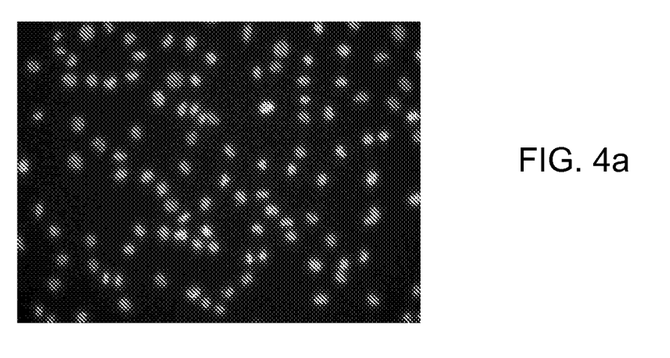
FIG. 4a-c illustrates a normal image, a defocused image and low content to noise ratio (CNR) image of a biological sample in accordance with the invention.
Figure 4B:
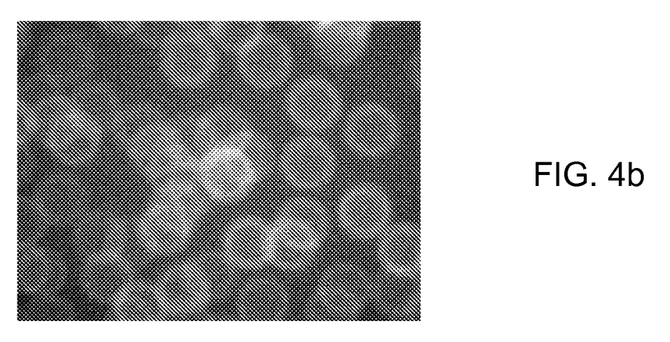
Figure 4C:
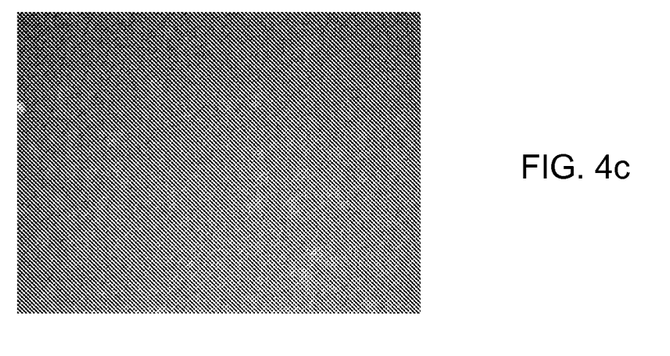

FIG. 4a shows an illustration of a normal image, a defocused image and a low content to noise (CNR) ratio image. The defocused image (4b) and the low CNR image (4c) can lead to a failure of segmentation and tracking routines. A defocused image indicates that there is a problem with the algorithm on the microscope. A defocused image is one that is out-of-focus. In simple terms, focus can be defined as the state of maximum distinctness or clarity of the sample or sample feature to be imaged. [0]A defocused image is an image that looks blurry or out-of-focus because the imaging plane is not located in the same plane as the sample of interest. A low contrast to noise ratio image indicates there is a problem with protocol or lens of the microscope. Many things can contribute to low CNR, including: low concentration of contrast agent (e.g. fluorescent probe), degradation of contrast agent or its target, improper focus, high background signal from the sample (e.g. unincorporated probe), insufficient exposure time, over-exposure, lens aberrations, dirt on the lens, dirt on the sample support (e.g. fingerprint on the plate bottom), artifacts in the sample (e.g. dust) that obscure the true signal, etc. basically, contributing factors can come the various elements that comprise the total system—e.g. the probe, the sample, the sample support, the acquisition conditions, the detection system. In order to prevent the failure of segmentation and tracking, the associated algorithm, routine, software or equation described in FIG. 3 is utilized to detect automatically images that are defocused or have a low CNR, so that aberrant images can be removed from analysis before segmentation and tracking occur. Also, the algorithm finds when the CNR is not low but too low for downstream processing.

Returning to FIG. 3, at block 305 a wavelet transform, Fourier transform, or other standard frequency decomposing transform is applied to the image of the at least one cell. Wavelets use a pair of filters including a filter that consists of the low-pass filter coefficients, h(k), and the high-pass filter coefficients, $g(k)=(-1)^{k+1} h(L+1-k)$, where $k=1 \ldots L$ represents the level of the decomposition, and L is the number of levels. These functions are constructed by translating and dilating a single mother wavelet, which is localized in both the spatial and frequency domain. The mother wavelet is constructed from the scaling function as $$\varphi(x) = \sqrt{2} \sum_{k=-\infty}^{\infty} h(k)\varphi(2x-k) \qquad (1)$$

$$\psi(x) = \sqrt{2} \sum_{k=-\infty}^{\infty} g(k)\varphi(2x-k)$$

Figure 5:
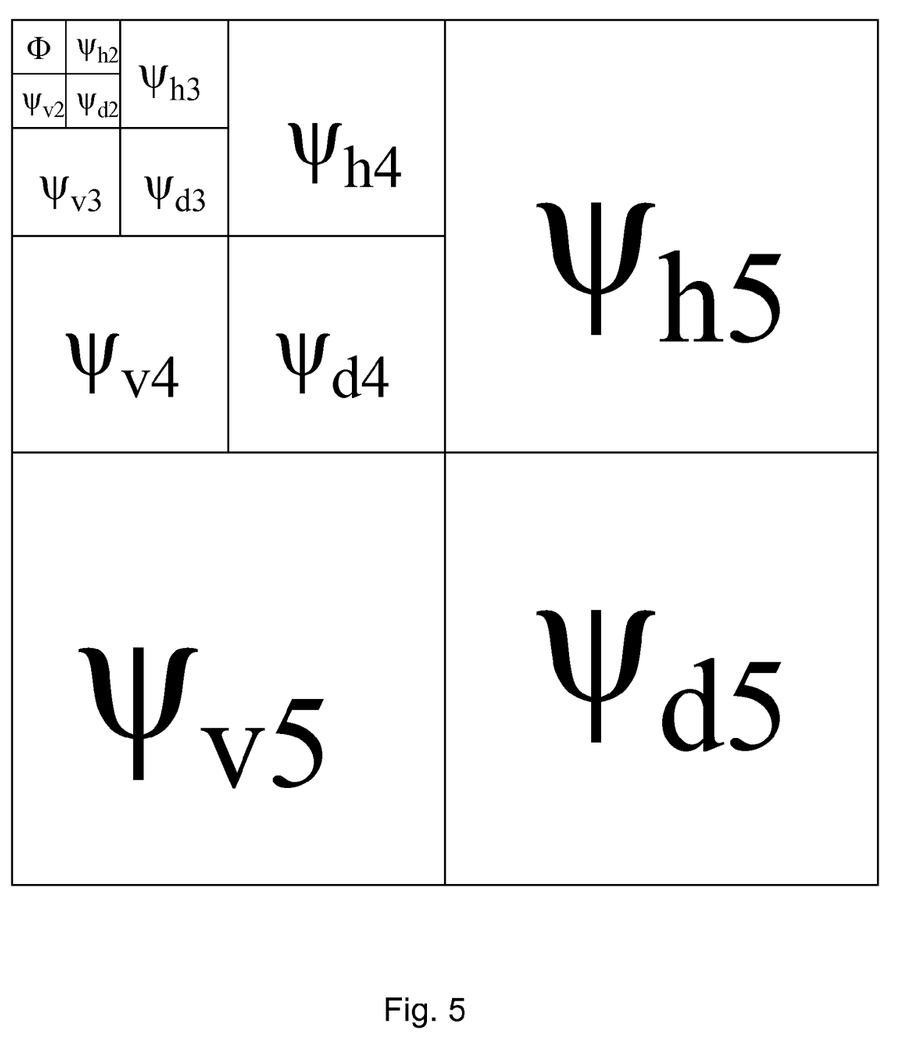
FIG. 5 illustrates a wavelet decomposition for 5 levels in accordance with the invention.

To apply this wavelet decomposition to 2D signals, separable 2D filters can be obtained from the successive 1D filtering using the scaling functions in Equation 1. Such operations result in one approximation channel and three detail channels $$\phi(i,j)=\phi(i)\phi(j)$$

$$\psi_h(i,j)=\phi(i)\psi(j)$$

$$\psi_v(i,j)=\psi(i)\phi(j)$$

$$\psi_d(i,j)=\psi(i)\psi(j) \qquad (2)$$

where i is the x index and j is the y index. The intuition of the operations in Equation 2 is that the $\phi$ performs low-pass filtering in both x and y leading to a smooth version of the original, $\psi_1$ performs low-pass filtering in x and high-pass filtering in y leading to horizontal edges, $\psi_2$ leads to vertical edges, and $\psi_3$ leads to diagonal edges. At successive iterations of the decomposition, the low-pass image is further decomposed into four channels, and the resulting images at each level are decimated or sub-sampled by 2. An example of the wavelet decomposition can be seen in FIG. 5, where the subscripts on each of the $\psi$ refer to level of the decomposition. For this FIG. 5, the wavelet decomposition is for 5 levels, where the wavelets are shown as a plurality of sub-images. The plurality of sub-images has a plurality of low frequency channels for a first and second plurality of sub-images, a plurality of middle frequency channels for a third and fourth plurality of sub-images and a plurality of high frequency channels for a fifth plurality of sub-images. In another embodiment of this invention, more or less than 5 levels of wavelet or plurality of sub-images may be decomposed. Each of the channels is identified as either an approximation channel ($\phi$) or a detail channel ($\psi$). Each detail channel is indicated by a subscript letter as defined in Equation 2 and by a number indicating the level of decomposition, with lower values representing lower frequencies. There is only one approximation channel.

Using the wavelet decomposition, the energy in each channel provides insight into the texture of the image. Smooth images tend to concentrate most of the energy in the low frequency channels, whereas the wavelet decomposition of textured images show energy spread throughout the channels as stated in article by Porter R. Canagarajah, C. N., which is hereby incorporated by reference. Porter, R., Canagaraja, C. N.: *A Robust Automatic Clustering Scheme for Image Segmentation using Wavelets*. IEEE Transactions on Image processing 5(4) (1996) pages 662-665. For the application of defocused images, the high-frequency noise is still present and thus provides little discriminative information. However the middle frequencies are attenuated relative to in-focus images. Using this information in block 305, we calculate the defocus ratio $R_d$ of the lower frequency channel to the middle frequency channels as $$R_d = \frac{E(\varphi)}{E(\psi_{h1}) + E(\psi_{v1}) + E(\psi_{d1}) + E(\psi_{h2}) + E(\psi_{v2}) + E(\psi_{d2})} \qquad (3)$$

where E(.) represents the energy operator, and the numbers represent the level of the decomposition, with lower numbers signifying lower frequencies. The energy is defined to be the mean magnitude of the wavelet coefficients for that sub-band $$E(x) = \frac{1}{IJ} \sum_{i=1}^{I} \sum_{j=1}^{J} |x(i,j)|, \qquad (4)$$

where IJ is the number of coefficients in channel x, and x(i,j) is the value of the coefficient. Using this defocus ratio, it is possible to distinguish between focused and defocused images: for defocused images, the ratio is high, and vice versa for focused images.

As a helpful side-effect, the ratio also finds images with low contrast-to-noise since the middle frequency energy in these images is also low relative to the low frequency energy. While it is desirable to find these images as well, it is helpful to separate them from defocused images since this gives additional feedback to the user or, potentially, to the microscope. In block 305, an information entropy H(X) measure is utilized to separate these since the intensity distributions of the low contrast images are more uniform than those with high contrast.

$$H(X) = -\sum_{i=1}^{n} p(x_i) \log_2 p(x_i). \qquad (5)$$

Here, X is a discrete random variable that can take on possible values $(x_1, \ldots x_n)$ corresponding to the bins of the standard probability density function of the image intensities. Due to the randomness in images with low contrast-to-noise, they have a lower entropy score than high contrast-to-noise images, even defocused images. Next, at block 305 there is a comparison between the calculated values of entropy and defocus ratio with predetermined test values that may be stored in the processor. Based on this comparison it will be shown if the image is corrupted. After the low contrast-to-noise image is separated from the de-focused image, then at block 309 the process discards or removes the image, then the process returns to block 301 where a next image is received in sequence.

To summarize, the wavelet energy score is used to separate normal images from defocused images. Next, the defocused images are separated into those that are truly defocused and those with low contrast-to-noise using the entropy measure.

This sequence can be seen in the flow chart of FIG. 3. Those images that pass these tests continue to the segmentation and tracking stages of block 305.

The defocus and low CNR detection algorithms were used as a pre-processing module of the cell tracking system described in FIG. 3. The aforementioned algorithms were run on a set of 4384 images under various experimental setups and different cell treatments and consisting of a mixture of defocused images and images with low CNR. Each of these images was manually annotated as to whether it was defocused, had low CNR, or was normal; in total, there were 190 defocused images, 100 low CNR images, and 4094 normal images.

Figure 6A:
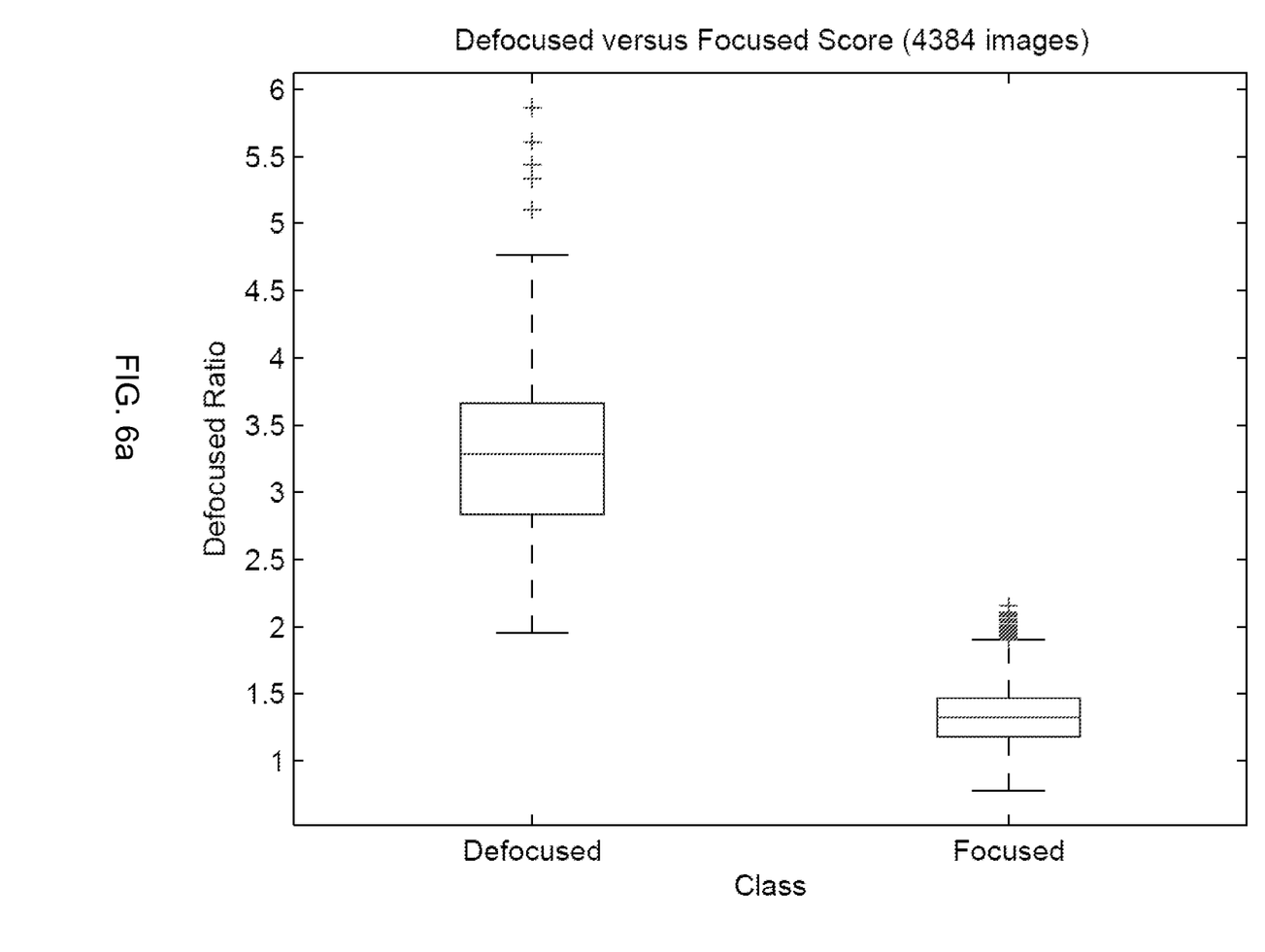
FIGS. 6(a) and 6(b) are graphical representations of statistical results of defocus and low-CNR detection images in accordance with the invention.
Figure 6B:
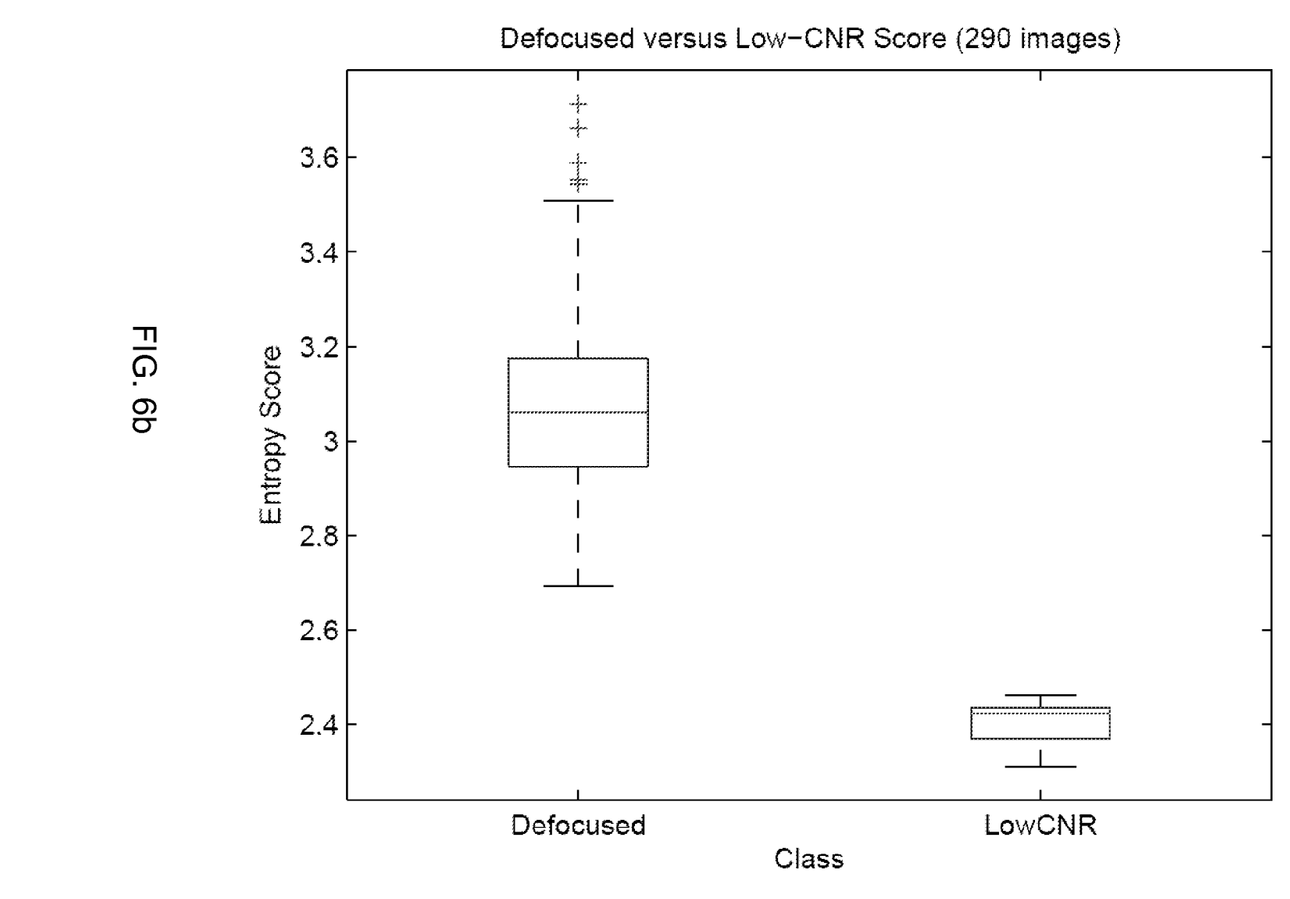

FIG. 6(a) gives a box-plot of the defocus score for the defocused versus the normal images. The algorithm clearly separates the two classes; a threshold of 2 results in 1 missed detection (0.03% error) and 21 false positives (<5% error). FIG. 6(b) shows a box-plot of the entropy measure for the defocused versus the low-CNR images. The algorithm separates the two classes effectively, and results in perfect separation for a threshold of 2.5.

The combination of these algorithms yields effective defocus and low-CNR detection for all 4384 images. The algorithm was also tested on a dataset taken from a different modality with a different microscope. These phase-contrast images displayed occasional defocus drift. Using the same parameters as above, the algorithms were able to separate all of the 300 images in this experiment into their correct focus/defocus classes.

Once the defocused and low-CNR images were removed, the cell segmentation and tracking algorithms were applied to the datasets. The algorithms were applied to four datasets— two with no treatment (control), and two treated with Roscovitine. Nuclei were stained with a relatively low concentration of the nuclear DNA stain Hoechst™33342 to aid identification.

Figure 7:
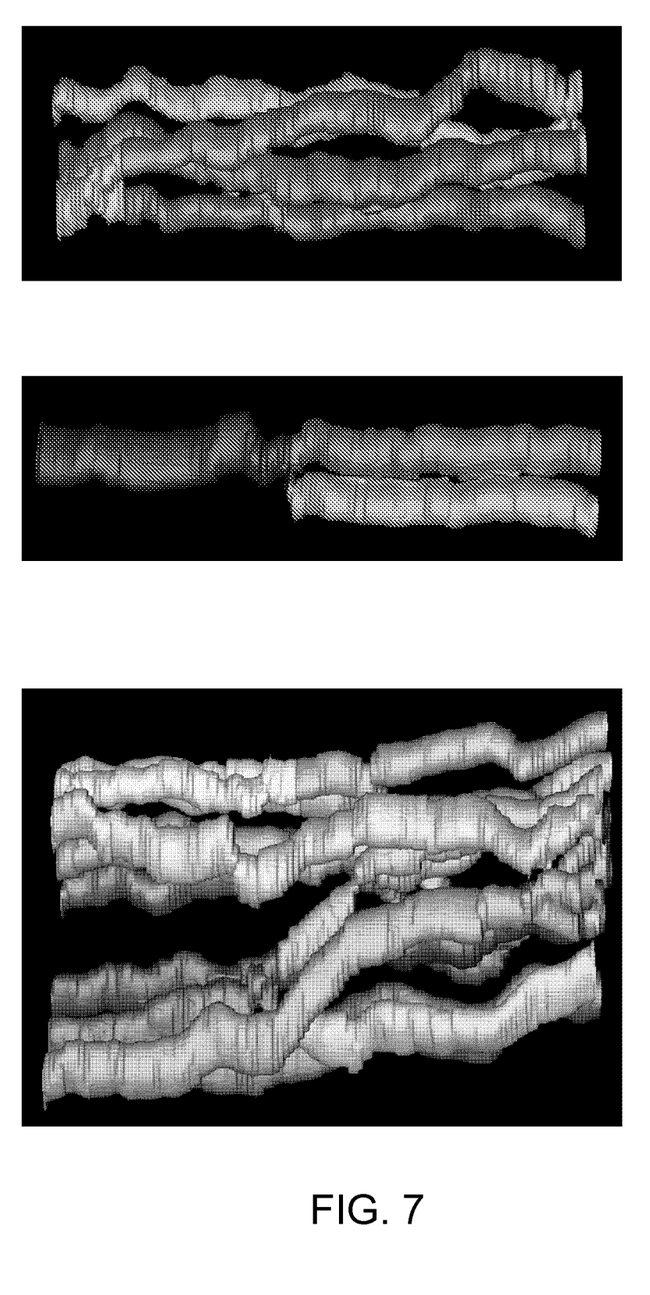
FIG. 7 is a graphical illustration of Spatio-Temporal Trees in accordance with the invention.

FIG. 7 shows several examples of spatio-temporal trees extracted by the algorithms. The aforementioned algorithms are related to segmentation and tracking. Although the cells move in clusters, touch one another, and undergo mitosis, the algorithms are able to successfully separate the clusters into individual tracks. These figures show that the algorithm can extract not only the tracks, but also the shape of the cells over time. The distance was calculated from manually placed centroids to the centroids of the automatically segmented cells for every cell of one of the experiments. The mean distance was 5.5 μm, and the standard deviation was 6.8 μm; the average cell diameter in these experiments was approximately 35 μm. The total number of manually identified cells was 6157, and 5758 were detected automatically, so that only 6% of the cells were under-segmented.

In order to denoise the images and segment the cells as disclosed in block 307 above, the standard cell segmentation algorithms are utilized. For example, an algorithm based on the shift invariant wavelet frames transformation of the image as well as the filtering of non-salient wavelet coefficients is utilized.

Prior research on biomedical data in articles by Genevesio et al. and Olivio-Marin J., which are incorporated by reference, demonstrates that the à trous (with holes) wavelet transform is robust to local noise variations and discards low frequency objects in the background. Genovesio, A., Liedl, T, Emiliani, V., Parak, W. J., Coppey-Moisan, M., Olivo-Main J.: *Multiple particle tracking in 3−d+t microscopy: method and application to the tracking of endocytosed quantum dots.* IEEE Trans. Image Proc. 15(5) (2006) pages 1062-1070 and Olivo-Marin, J.: *Automatic detection of spots in biological images by a wavelet-based selective filtering technique.* In ICIP (1996)1: pages 311-314. The decomposition is represented as $$I_i(x, y) = \sum_{m,n} h(m, n) I_{i-1}(x - 2^{i-1}m, y - 2^{i-1}n) \quad (6)$$

$$W_i(x, y) = I_i(x, y) - I_{i+1}(x, y) \quad (7)$$

where $I_i$ and $W_i$ represent the approximation and detail images, respectively, at each scale, i, and h(m,n) denotes the scaling function.

Assuming that the image noise is additive, the corresponding wavelet transformation results in coefficients generated by the underlying signal $W^s$ and those that correspond to image noise $W^N$. To approximate the signal term, we threshold the image stack with an Amplitude-scale-invariant Bayes Estimator (ABE) using Jeffreys' non-informative prior given scale i and position (x,y)

$$W_i^I(x, y) \approx \delta^{ABE}(W_i(x, y)) = \frac{(W_i(x, y)^2 - 3\sigma_i^2)_+}{W_i(x, y)} \quad (8)$$

where $\sigma_i^2$ is the estimated noise variance at a given scale. In order to further reduce noise and enhance objects that extend across multiple resolutions, a correlation stack is computed $C_s(x,y)$, which is the multiplication of a subset of the denoised wavelet coefficients corresponding to the selected scales $$C_s(x, y) = \prod_{i=j_l}^{j_s} W_i^I(x, y)_+. \quad (9)$$

The segmentation is then obtained as the extraction of connected regions in the correlation stack. FIG. 8 shows an example segmentation of a low-dose Hoechst-stained section, demonstrating the accuracy of the segmentation approach even with a very low contrast-to-noise ratio. This shows that, even if some low-CNR images are passed by the low-CNR detection algorithms, they can be handled by the segmentation module, although the results are generally not as clean as with images with higher CNR. The segmented spatio-temporal volume is then labeled in 3D. This results in a 3D set of segmented "tubes" corresponding to cells moving through time.

The 3D labeled "tubes" comprise two types of tracks: those corresponding to single cells (single-tracks) and those corresponding to multiple cells clustered together (multi-tracks). The goal of the spatio-temporal cluster segmentation step is to segment the multi-tracks into individual tracks by utilizing learned object descriptors. The distribution p of learned features that capture the appearance of cells $f_i^t$ (where i is the cell number and t is the time slice) can be readily trained from the single-tracks. Alternatively, if few single-tracks are present in the dataset, these features can be trained using other datasets, assuming that the experimental conditions are kept constant.

Once the multi-tracks have been identified, the cell clusters are segmented by taking advantage of temporal context for determining the best way to split cells. There is a determination of whether an object should be split into individual cells or a set of objects should be merged to form a cell. The temporal information is utilized by propagating higher likelihood cell segmentations to slices with lower likelihood. We incorporate a statistical test to determine which segmented objects should be propagated across slices, and we use a curve evolution algorithm that finds the best segmentation such that it retains the relative area of the cell regions across slices.

For a given multi-track, the algorithm propagates the segmented objects from slices with greater number of objects to those with fewer. At the completion of the curve evolution, the number of objects on the adjacent frame will be the same as the reference frame, and at least one object will have been segmented. The features $f_i^t$ of each of the split segments are then used to calculate the likelihood of the segment being cell-like using the trained distribution parameters $\mu$ and $\Sigma$ $$G(f_i^t) \propto \exp\left[-\frac{1}{2}(f_i^t - \mu)^T \sum\nolimits^{-1} (f_i^t - \mu)\right] \quad (10)$$

Given the curve evolution, the likelihoods, and the fact that the reference frame has more objects than the adjacent frame, we can determine whether to merge the labels on the reference frame or split the labels on the adjacent frame by comparing the likelihood of the full object to the average of its parts $$L_{merge} = G(f_{i \in I}^t) - \frac{1}{|I|} \sum_{i \in I} G(f_i^t) \quad (11)$$

$$L_{split} = \frac{1}{|I|} \sum_{i \in I} G(f_i^{t+o}) - G(f_{i \in I}^{t+o}) \quad (12)$$

where o is an offset from the reference frame, and I is the set of labels under consideration for merging/splitting. If $L_{merge} > L_{split}$, the labels are merged on the reference frame; otherwise they are split on the adjacent frame. $L_{merge}$ is high when the combined labels on the reference frame have a higher likelihood than the separate labels, and $L_{split}$ is high when the separate labels on the adjacent frame have higher likelihood than when they are combined circumstances, when one is positive, the other will be negative, and the final decision combines both measures.

In this process mitosis is a special case, since a cell will be one object in one frame and two in the next. This case is handled implicitly by leaving the regions unchanged if both splitting the cell on the previous frame and merging the cells on the next frame lead to lower likelihoods. Here, the causal relationships are also taken into account since cells can split over time but not merge.

The step of renumbering the cells in the clusters to correctly associate cells across frames is accomplished using the parameters $\mu_d$, $\Sigma_d$ of a distribution trained from the single-tracks. The features $f_j^{t+1}$ with j=1:L of all cells on the next slice are compared to the features of each of the cells on the current slice $f_i^t$ with i=1:L using $\mu_d$ and $\Sigma_d$ $$G(d_{i,j}^t) \propto \exp\left[-\frac{1}{2}(d_{i,j}^t - \mu_d)^T \sum\nolimits_{d}^{-1} (d_{i,j}^t - \mu_d)\right] \quad (13)$$

where $d_{i,j}^t = |f_i^t - f_i^{t+1}|$ is the absolute difference between the feature vectors. Using the assignment from the Hungarian algorithm that provides the optimal assignment from cells across frames, the cell labels are matched across the slices.

This invention provides a system and method that allows a user to determine if there are abnormalities in an image. If there are abnormalities in the image, then the user is able to determine what type of corruption is in the image. The user is able to quickly determine if there is an abnormal image in order to remove the image before it undergoes cell segmentation and tracking algorithm. The user is able to easily optimize the imaging conditions for viewing the image of the cell(s) by quickly determining if the image has a corruption and removing the image. Thus, this invention provides the user with a means to easily optimize the imaging conditions for experimentation.

Although the present invention has been described above in terms of specific embodiments, many modification and variations of this invention can be made as will be obvious to those skilled in the art, without departing from its spirit and scope as set forth in the following claims.

What is claimed is:

1. A method of analyzing a plurality of images of a biological sample comprising a population of at least one cell from time-lapse imaging, comprising the steps of:
    detecting out of focus images by:
    decomposing each image, using a wavelet transform, Fourier transform, or other frequency decomposing transform, into a plurality of sub-images each representing a specific frequency channel and one sub-image representing an approximation channel,
    calculating a defocus ratio for each image as the ratio between the energy of the approximation channel sub-image and the sum of the energy of the sub-images representing middle frequency channels, and
    comparing the defocus ratio of each image with a predetermined defocus threshold value wherein images with a defocus ratio exceeding the defocus threshold value are identified as out of focus, and
    segmenting and tracking the at least one cell in images not identified as out of focus; wherein each image is decomposed using a wavelet transform and the energy of the sub-images is defined as the mean magnitude of wavelet coefficients for each sub-image.

2. The method according to claim 1 further comprising the steps of:
    detecting images with low contrast-to-noise ratio,
    calculating an information entropy measure defining the degree of randomness for each image
    comparing the information entropy measure for each image with a predetermined entropy threshold value, wherein images with an information entropy measure below the entropy threshold value are identified as low contrast-to-noise images,
    and wherein the step of segmenting and tracking is performed on images not identified as out of focus or as low contrast-to-noise images.

3. The method according to claim 1 wherein the wavelets involves use of a pair of filters including a filter that consists of the low-pass filter coefficients, h(k) and the high-pass filter coefficients, g(k)=$(-1)^{k+1}$h(L+1-k), where k=1 ... L represents the level of the decomposition, and L is the number of levels, and wherein the mother wavelet is constructed from the scaling function as:

$$\varphi(x) = \sqrt{2} \sum_{k=-\infty}^{\infty} h(k)\varphi(2x - k)$$

-continued $$\psi(x) = \sqrt{2} \sum_{k=-\infty}^{\infty} g(k)\varphi(2x-k)$$

providing for one approximation channel and three detail channels $$\phi(i,j)=\phi(i)\phi(j)$$

$$\psi_h(i,j)=\phi(i)\psi(j)$$

$$\psi_v(i,j)=\psi(i)\phi(j)$$

$$\psi_d(i,j)=\psi(i)\psi(j)$$

where i is the x index and j is the y index,
and wherein the defocus ratio $R_d$ is calculated as $$R_d = \frac{E(\varphi)}{E(\psi_{h1})+E(\psi_{v1})+E(\psi_{d1})+E(\psi_{h2})+E(\psi_{v2})+E(\psi_{d2})}$$

where E(.) represents the energy operator:

$$E(x) = \frac{1}{IJ}\sum_{i=1}^{I}\sum_{j=1}^{J} |x(i,j)|,$$

where IJ is the number of coefficients in channel x, and x(i,j) is the value of the coefficient, and the numbers represent the level of the decomposition, with lower numbers signifying lower frequencies.

4. The method according to claim 2 wherein the calculation of the information entropy measure is denoted as H(X), and is calculated by:

$$H(X) = -\sum_{i=1}^{n} p(x_i)\log_2 p(x_i).$$

wherein X is a discrete random variable that can take on possible values $(x_1, \ldots x_n)$ corresponding to the bins of the standard probability density function of the image intensities.

5. A system for analyzing a plurality of images of a biological sample comprising a population of at least one cell from time-lapse imaging, the system comprising a microscope system and an image receiving device arranged to:
  detect out of focus images by:
  decomposing each image, using a wavelet transform, Fourier transform, or other frequency decomposing transform, into a plurality of sub-images each representing a specific frequency channel and one sub-image representing an approximation channel,
  calculating a defocus ratio for each image as the ratio between the energy of the approximation channel sub-image and the sum of the energy of the sub-images representing middle frequency channels, and
  comparing the defocus ratio of each image with a predetermined defocus threshold value wherein images with a defocus ratio exceeding the defocus threshold value are identified as out of focus, and
  segment and track the at least one cell in images not identified as out of focus; wherein each image is decomposed using a wavelet transform and the energy of the sub-images is defined as the mean magnitude of wavelet coefficients for each sub-image.

6. The system according to claim 5 further comprising the steps of:
  detecting images with low contrast-to-noise ratio,
  calculating an information entropy measure defining the degree of randomness for each image
  comparing the information entropy measure for each image with a predetermined entropy threshold value, wherein images with an information entropy measure below the entropy threshold value are identified as low contrast-to-noise images,
  and wherein the step of segmenting and tracking is performed on images not identified as out of focus or as low contrast-to-noise images.

7. The system according to claim 5 wherein the wavelets involves use of a pair of filters including a filter that consists of the low-pass filter coefficients, h(k), and the high-pass filter coefficients, $g(k)=(-1)^{k+1}h(L+1-k)$, where k=1 . . . L represents the level of the decomposition, and L is the number of levels, and wherein the mother wavelet is constructed from the scaling function as:

$$\varphi(x) = \sqrt{2} \sum_{k=-\infty}^{\infty} h(k)\varphi(2x-k)$$

$$\psi(x) = \sqrt{2} \sum_{k=-\infty}^{\infty} g(k)\varphi(2x-k)$$

providing for one approximation channel and three detail channels $$\phi(i,j)=\phi(i)\phi(j)$$

$$\psi_h(i,j)=\phi(i)\psi(j)$$

$$\psi_v(i,j)=\psi(i)\phi(j)$$

$$\psi_d(i,j)=\psi(i)\psi(j)$$

where i is the x index and is the y index,
and wherein the defocus ratio $R_d$ is calculated as $$R_d = \frac{E(\varphi)}{E(\psi_{h1})+E(\psi_{v1})+E(\psi_{d1})+E(\psi_{h2})+E(\psi_{v2})+E(\psi_{d2})}$$

where E(.) represents the energy operator:

$$E(x) = \frac{1}{IJ}\sum_{i=1}^{I}\sum_{j=1}^{J} |x(i,j)|,$$

where IJ is the number of coefficients in channel x, and x(i,j) is the value of the coefficient, and the numbers represent the level of the decomposition, with lower numbers signifying lower frequencies.

8. The system according to claim 7 wherein the calculation of the information entropy measure is denoted as H(X), and is calculated by:

$$H(X) = -\sum_{i=1}^{n} p(x_i)\log_2 p(x_i),$$

wherein X is a discrete random variable that can take on possible values $(x_1, \ldots x_n)$ corresponding to the bins of the standard probability density function of the image intensities.

* * * * *